United States Patent

Nakatsuka et al.

Patent Number: 5,346,878
Date of Patent: Sep. 13, 1994

[54] RECORDING MATERIAL

[75] Inventors: Masakatsu Nakatsuka, Kanagawa; Naomasa Koike; Akinori Okada, both of Tokyo, all of Japan

[73] Assignees: Mitsui Toatsu Chemicals, Inc.; Mitsubishi Paper Mills Limited, both of Tokyo, Japan

[21] Appl. No.: 108,500

[22] Filed: Aug. 18, 1993

Related U.S. Application Data

[63] Continuation-in-part of Ser. No. 946,694, Sep. 18, 1992, Pat. No. 5,306,688.

[30] Foreign Application Priority Data

Sep. 24, 1991 [JP] Japan ................................. 3-243201
Jun. 26, 1992 [JP] Japan ................................. 4-168744
Nov. 6, 1992 [JP] Japan ................................. 4-297027

[51] Int. Cl.$^5$ ............................................. B41M 5/30
[52] U.S. Cl. ..................................... 503/209; 503/210; 503/211; 503/212; 503/216; 503/225
[58] Field of Search ............................. 427/150-152; 503/208, 209, 216, 225, 210-212

[56] References Cited

U.S. PATENT DOCUMENTS 4,824,824 4/1989 Matsushita et al. ............... 503/204
4,992,411 2/1991 Okhuru ............................ 503/200

FOREIGN PATENT DOCUMENTS 0253666 1/1988 European Pat. Off. ............ 503/216

Primary Examiner—B. Hamilton Hess
Attorney, Agent, or Firm—Millen, White, Zelano, & Branigan

[57] ABSTRACT

The heat-sensitive recording material disclosed comprises a colorless or pale colored dyestuff precursor, one or more salicylic acid derivative of the formula (1) or metal salt of the derivative and an aliphatic amide compound having 18~60 carbon atoms in molecular structure, and is excellent in thermal response and preservation stability of white portions and images.

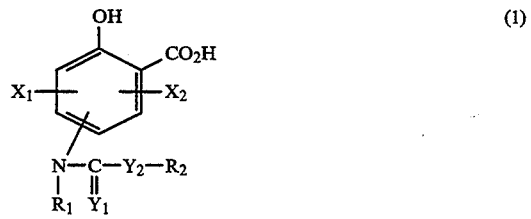

(1)

wherein $X_1$ and $X_2$ are a hydrogen atom, a halogen atom, an alkyl group, an alkoxy group, an aralkyl group or an aryl group, $Y_1$ and $Y_2$ are an oxygen atom or a sulfur atom, $R_1$ is a hydrogen atom, an alkyl group, an aralkyl group or an aryl group, and $R_2$ is an alkyl group, an alkenyl group, an aralkyl group or an aryl group.

20 Claims, No Drawings

RECORDING MATERIAL

CROSS REFERENCE TO RELATED APPLICATION

This is a continuation-in-part of our application Ser. No. 946,694 filed Sep. 18, 1992, now U.S. Pat. No. 5,306,688.

BACKGROUND OF THE INVENTION

1. Field of the Invention

The present invention relates to a heat-sensitive recording material and particularly relates to a heat-sensitive recording material which is particularly excellent in thermal response and preservation stability of white portions and images.

2. Related Art of the Invention

Heat-sensitive recording materials generally have a heat-sensitive recording layer on a substrate and the recording layer comprises as principal components a usually colorless or pale colored dyestuff precursor which is the electron donor and a developer which is an electron acceptor. When the recording materials are heated with a thermal head, hot-pen or laser beam, recording images can be obtained by an instantaneous reaction between the dyestuff precursor and the developer.

These recording materials are disclosed, for example, in Japanese Patent Publication SHO 43-4160 and 45-14039, and have advantages that a record can be obtained with relatively simple equipment, maintenance can be conducted with ease, and noise is inhibited. As a result, these heat-sensitive recording materials are used in a broad range of fields such as measuring instrument recorders, facsimiles, printers, computer terminals, labels and automatic ticket vendors.

Heat-sensitive recording materials obtained by using conventional, electron donating colorless dyestuff precursors and electron accepting compounds have characteristics such as high color density. On the other hand, these recording materials have disadvantages that recorded images fade away when they are kept in contact with plastics such as polyvinyl chloride as plasticizers and additives that are usually contained in them migrate to the recording materials, that the preservation characteristic of the recorded images is inferior because the color of these images is deteriorated by contact with chemicals contained in food and cosmetics, or that the color of marks put on them using a marker on white portions change or marking causes color development. Consequently, these recording materials are restricted in the field of use, and improvement of these recording materials has been strongly desired.

As a means for improving the preservation characteristic of the recorded images and white portions, heat-sensitive recording materials using as the electron accepting compound salicylic acid derivatives having a substituent such as an alkyl group, aralkyl group, alkyloxy group, and aryl group or using metal salts thereof have been proposed in Japanese Laid-Open Patent SHO 62-169681, 63-22683 and 63-95977.

However, the salicylic acid derivatives described in these patents provide unsatisfactory preservation characteristic of developed images, insufficient preservation stability of white portions, and additionally low coloring sensitivity. Thus, these salicylic acid derivatives have been difficult to serve as heat-sensitive recording materials in practical high speed recording.

SUMMARY OF THE INVENTION

The object of the invention is to provide a heat-sensitive recording material having excellent thermal response and preservation stability of white portions and images.

The aspect of the invention is a heat-sensitive recording material having a usually colorless or pale colored dyestuff precursor and an electron accepting compound which develops color of said dyestuff precursor by heat-reaction, comprising one or more compounds selected from a salicylic acid derivative represented by the formula (1):

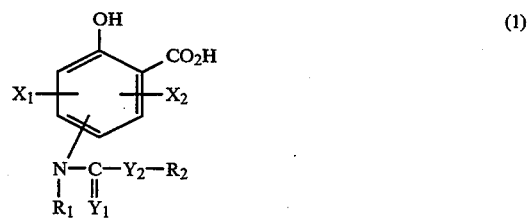

wherein $X_1$ and $X_2$ are a hydrogen atom, a halogen atom, an alkyl group, an alkoxy group, an aralkyl group, or an aryl group, $Y_1$ and $Y_2$ are an oxygen atom or a sulfur atom, $R_1$ is a hydrogen atom, an alkyl group, an aralkyl group or an aryl group, and $R_2$ is an alkyl group, an alkenyl group, an aralkyl group or an aryl group, or a divalent, trivalent or tetravalent metal salt of said salicylic acid derivative, further comprising an aliphatic amide compound having 18~60 carbon atoms in molecular structure and being excellent in thermal response and preservation stability of white portions and images.

The heat-sensitive recording material of the invention is prepared by using the salicylic acid derivative of the formula (1) or the metal salt of the derivative in combination with the aliphatic amide compound having 18~60 carbon atoms in the molecular structure, and has further improved thermal response in addition to thermal response and preservation stability of developed images which are essential properties of the salicylic acid derivative of the formula (1) or the metal salt of the derivative as the electron accepting compound for use in the heat-sensitive recording material.

That is, the invention provides a heat-sensitive recording material which is particularly excellent in thermal response, also excellent in preservation stability of white portions and images, and can be compatible with practical high speed recording.

DETAILED DESCRIPTION OF THE INVENTION

The principal electron accepting compound used in the invention is a salicylic acid derivative represented by the formula(1) and/or a metal salt of the salicylic acid derivative.

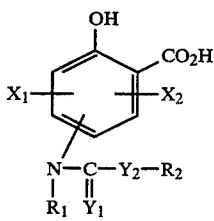

(1)

wherein $X_1$ and $X_2$ are a hydrogen atom, a halogen atom, an alkyl group, an alkoxy group, an aralkyl group or an aryl group, $Y_1$ and $Y_2$ are an oxygen or a sulfur atom, $R_1$ is a hydrogen atom, an alkyl group, an aralkyl group or an aryl group, and $R_2$ is an alkyl group, an alkenyl group, an aralkyl group or an aryl group.

The salicylic acid derivative and the metal salt of the derivative which can be used in the invention have following atoms and groups in the formula(1).

$X_1$ and $X_2$ are a hydrogen, an alkyl, alkoxy, aralkyl or aryl group or halogen atom, preferably hydrogen, $C_1 \sim C_{20}$ alkyl, $C_5 \sim C_{14}$ alicyclic, $C_1 \sim C_{20}$ alkoxy, $C_7 \sim C_{20}$ aralkyl, phenyl, fluorine, chlorine or bromine, more preferably hydrogen, $C_1 \sim C_4$ alkyl, cyclohexyl, $C_1 \sim C_4$ alkoxy, benzyl, a -methylbenzyl, cumyl, phenyl or chlorine, and most preferably hydrogen.

$Y_1$ and $Y_2$ are a oxygen or sulfur atom, and preferably $Y_1$ is oxygen.

$R_1$ is a hydrogen atom, an alkyl, aralkyl or aryl group, preferably hydrogen, $C_1 \sim C_{20}$ alkyl, $C_5 \sim C_{14}$ alicyclic, $C_7 \sim C_{20}$ aralkyl, phenyl or substituted phenyl, more preferably hydrogen, $C_1 \sim C_8$ alkyl, cyclopentyl, cyclohexyl, cycloheptyl, benzyl or phenyl, further preferably hydrogen, $C_1$-$C_4$ alkyl or phenyl, and most preferably hydrogen.

$R_2$ is an alkyl, alkenyl, aralkyl or aryl group, preferably alkyl or substituted alkyl, alicyclic or substituted alicyclic, alkenyl or substituted alkenyl, cyclic alkenyl or substituted cyclic alkenyl, aralkyl or substituted aralkyl, phenyl or substituted phenyl, naphthyl or substituted naphthyl, or heteroaromatic or substituted heteroaromatic.

The alkyl or alkenyl represented by $R_2$ can be monosubstituted or polysubstituted.

The substituents include, for example, $C_1 \sim C_{20}$ alkoxy, $C_2 \sim C_{20}$ alkoxyalkyloxy, $C_2 \sim C_{20}$ alkenyloxy, $C_7 \sim C_{20}$ aralkyloxy, $C_8 \sim C_{20}$ aralkyloxyalkoxy, $C_9 \sim C_{20}$ aryloxy, $C_1 \sim C_{20}$ aryloxyalkoxy, $C_8 \sim C_{20}$ arylalkenyl, $C_9 \sim C_{20}$ aralkylalkenyl, $C_1 \sim C_{20}$ alkylthio, $C_2 \sim C_{20}$ alkoxyalkylthio, $C_2 \sim C_{20}$ alkylthioalkylthio, $C_2 \sim C_{20}$ alkenylthio, $C_7 \sim C_{20}$ aralkylthio, $C_8 \sim C_{20}$ aralkyloxyalkylthio, $C_8 \sim C_{20}$ aralkylthioalkylthio, $C_6 \sim C_{20}$ arylthio, $C_7 \sim C_{20}$ aryloxyalkylthio, $C_7 \sim C_{20}$ arylthioalkylthio, hetroalicyclic and halogen.

Further, aryl which is included in these substituents can be substituted with $C_1 \sim C_6$ alkyl, $C_1 \sim C_6$ alkoxy, $C_1 \sim C_6$ alkylthio, $C_7 \sim C_{10}$ aralkyl, $C_7 \sim C_{10}$ aralkyloxy, hydroxyl or halogen.

The aralkyl or aryl represented by $R_2$ can be monosubstituted or polysubstituted.

Exemplary substituents include, $C_1 \sim C_{20}$ alkyl, $C_2 \sim C_{20}$ alkenyl, $C_7 \sim C_{20}$ aralkyl, $C_2 \sim C_{20}$ aryl, $C_1 \sim C_{20}$ alkoxy, $C_2 \sim C_{20}$ alkoxyalkyl, $C_2 \sim C_{20}$ alkoxyalkyloxy, $C_2 \sim C_{20}$ alkenyloxy, $C_3 \sim C_{20}$ alkenyloxyalkyl, $C_3 \sim C_{20}$ alkenyloxyalkyloxy, $C_7 \sim C_{20}$ aralkyloxy, $C_8 \sim C_{20}$ aralkyloxyalkyl, $C_8 \sim C_{20}$ aralkyloxyalkyloxy, $C_6 \sim C_{20}$ aryloxy, $C_7 \sim C_{20}$ aryloxyalkyl, $C_7 \sim C_{20}$ aryloxyalkyloxy, $C_2 \sim C_{20}$ alkylcarbonyl, $C_3 \sim C_{20}$ alkenylcarbonyl, $C_8 \sim C_{20}$ aralkylcarbonyl, $C_7 \sim C_{20}$ arylcarbonyl, $C_2 \sim C_{20}$ alkoxycarbonyl, $C_3 \sim C_{20}$ alkenyloxycarbonyl, $C_8 \sim C_{20}$ aralkyloxycarbonyl, $C_7 \sim C_{20}$ aryloxycarbonyl, $C_2 \sim C_{20}$ alkylcarbonyloxy, $C_3 \sim C_{20}$ alkenylcarbonyloxy, $C_8 \sim C_{20}$ aralkylcarbonyloxy, $C_7 \sim C_{20}$ arylcarbonyloxy, $C_{14} \sim C_{20}$ aralkyloxyaralkyl, $C_2 \sim C_{20}$ alkylthio, $C_7 \sim C_{20}$ aralkylthio, $C_6 \sim C_{20}$ arylthio, nitro, formyl, halogen, hydroxy and cyano.

Aryl which is present in these substituents can be further substituted with $C_1 \sim C_6$ alkyl, $C_1 \sim C_6$ alkoxy, $C_1 \sim C_6$ alkylthio, $C_7 \sim C_{10}$ aralkyl, $C_7 \sim C_{10}$ aralkyloxy, hydroxy or halogen.

Preferred $R_2$ is nonsubstituted or substituted alkyl having from 1 to 24 total carbon atoms, nonsubstituted or substituted alkenyl having from 2 to 24 total carbon atoms, nonsubstituted or substituted aralkyl having from 7 to 24 total carbon atoms, or nonsubstituted or substituted aryl having from 6 to 24 total carbon atoms.

The compound represented by the formula(1) in the invention has a carbamate group on a salicylic acid skeleton. The carbamate group is located on the position 3, 4, 5 or 6, preferably on the position 3, 4 or 5, most preferably on the position 4 or 5 in the salicylic acid skeleton. That is, a more preferred salicylic acid derivative is represented by the formula(2-a):

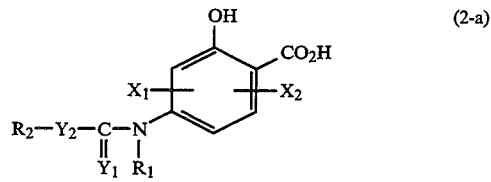

(2-a)

wherein $X_1$, $X_2$, $Y_1$, $Y_2$, $R_1$ and $R_2$ are the same as above, or by the formula(2-b):

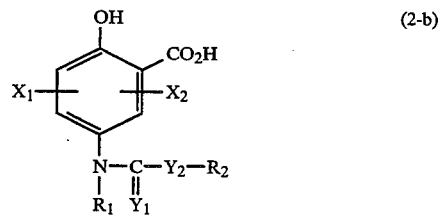

(2-b)

wherein $X_1$, $X_2$, $Y_1$, $Y_2$, $R_1$ and $R_2$ are the same as above.

A most preferred salicylic acid derivative is represented by the formula(2-c):

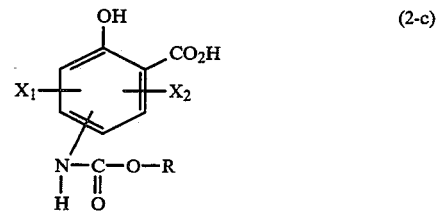

(2-c)

wherein X, and $X_2$ are the same as above, R is an alkyl group, an alkenyl group, an aralkyl group or an aryl group.

R in the formula (2-c) is an alkyl group such as methyl, ethyl, n-butyl, n-octyl, n-decyl, n-octadecyl, iso-butyl, isopentyl or cyclohexyl; an alkenyl group such as allyl; an aralkyl group such as benzyl or substituted benzyl; or an aryl group such as phenyl or substituted phenyl.

Exemplary salicylic acid derivatives represented by the formula(1) and the metal salts of the derivatives that can be used for the invention will be enumerated below. However, it is to be understood that the invention is not limited by the following compounds.

| No. | Compound |
|---|---|
| 1) | 3-(isopropyloxycarbonylamino)salicylic acid |
| 2) | 3-(isopentyloxycarbonylamino)salicylic acid |
| 3) | 3-(n-hexyloxycarbonylamino)salicylic acid |
| 4) | 3-(n-octyloxycarbonylamino)salicylic acid |
| 5) | 3-(n-decyloxycarbonylamino)salicylic acid |
| 6) | 3-[(4'-methylcyclohexyl)oxycarbonylamino]salicylic acid |
| 7) | 3-[(2'-cyclohexylethyl)oxycarbonylamino]salicylic acid |
| 8) | 3-(allyloxycarbonylamino)salicylic acid |
| 9) | 3-[(2'-hexenyl)oxycarbonylamino]salicylic acid |
| 10) | 3-[(2'-ethoxyethyl)oxycarbonylamino]salicylic acid |
| 11) | 3-[(3'-n-hexyloxypropyl)oxycarbonylamino]salicylic acid |
| 12) | 3-[(2'-benzyloxyethyl)oxycarbonylamino]salicylic acid |
| 13) | 3-(phenoxymethyloxycarbonylamino)salicylic acid |
| 14) | 3-[(2'-phenoxyethyl)oxycarbonylamino]salicylic acid |
| 15) | 3-[(2'-(4-chlorophenyl)oxyethyloxycarbonylamino]salicylic acid |
| 16) | 3-[2'-(4-methoxyphenyl)oxyethyloxycarbonylamino]salicylic acid |
| 17) | 3-[(2'-phenoxyethoxyethyl)oxycarbonylamino]salicylic acid |
| 18) | 3-(cinnamyloxycarbonylamino)salicylic acid |
| 19) | 3-[(2'-n-butylthioethyl)oxycarbonylamino]salicylic acid |
| 20) | 3-[(2'-methoxyethylthioethyl)oxycarbonylamino]salicylic acid |
| 21) | 3-[(2'-allylthioethyl)oxycarbonylamino]salicylic acid |
| 22) | 3-[(2'-benzylthioethyl)oxycarbonylamino]salicylic acid |
| 23) | 3-[(2'-phenylthioethyl)oxycarbonylamino]salicylic acid |
| 24) | 3-[(7'-chloroheptyl)oxycarbonylamino]salicylic acid |
| 25) | 3-(benzyloxycarbonylamino)salicylic acid |
| 26) | 3-[(4'-methylbenzyl)oxycarbonylamino]salicylic acid |
| 27) | 3-[(4'-chlorobenzyl)oxycarbonylamino]salicylic acid |
| 28) | 3-[(3'-phenoxybenzyl)oxycarbonylamino]salicylic acid |
| 29) | 3-(phenyloxycarbonylamino)salicylic acid |
| 30) | 3-[(2'-naphthyl)oxycarbonylamino]salicylic acid |
| 31) | 3-[(3'-furyl)oxycarbonylamino]salicylic acid |
| 32) | 3-[(3'-phenylphenyl)oxycarbonylamino]salicylic acid |
| 33) | 3-[(4'-methylphenyl)oxycarbonylamino]salicylic acid |
| 34) | 3-[(4'-n-butylphenyl)oxycarbonylamino]salicylic acid |
| 35) | 3-[(4'-tert-butylphenyl)oxycarbonylamino]salicylic acid |
| 36) | 3-[(4'-cylohexylphenyl)oxycarbonylamino]salicylic acid |
| 37) | 3-[(3'-methoxyphenyl)oxycarbonylamino]salicylic acid |
| 38) | 3-[(4'-n-butoxyphenyl)oxycarbonylamino]salicylic acid |
| 39) | 3-[(4'-n-octyloxyphenyl)oxycarbonylamino]salicylic acid |
| 40) | 3-[(4'-phenoxyphenyl)oxycarbonylamino]salicylic acid |
| 41) | 3-[(2'-acetylphenyl)oxycarbonylamino]salicylic acid |
| 42) | 3-[(4'-allylcarbonylphenyl)oxycarbonylamino]salicylic acid |
| 43) | 3-[(4'-phenylcarbonylphenyl)oxycarbonylamino]salicylic acid |
| 44) | 3-[(4'-n-butoxycarbonylphenyl)oxycarbonylamino]salicylic acid |
| 45) | 3-[(4'-benzyloxyphenyl)oxycarbonylamino]salicylic acid |
| 46) | 3-[(4'-acetyloxyphenyl)oxycarbonylamino]salicylic acid |
| 47) | 3-[(4'-ethylthiophenyl)oxycarbonylamino]salicylic acid |
| 48) | 3-[(4'-fluorophenyl)oxycarbonylamino]salicylic acid |
| 49) | 3-[(4'-chlorophenyl)oxycarbonylamino]salicylic acid |
| 50) | 3-[(4'-nitrophenyl)oxycarbonylamino]salicylic acid |
| 51) | 3-[(4'-forlphenyl)oxycarbonylamino]salicylic acid |
| 52) | 3-[(4'-hydroxyphenyl)oxycarbonylamino]salicylic acid |
| 53) | 3-[(4'-cyanophenyl)oxycarbonylamino]salicylic acid |
| 54) | 3-[(2',4'-dimethylphenyl)oxycarbonylamino]salicylic acid |
| 55) | 3-[(3',5'-dichlorophenyl)oxycarbonylamino]salicylic acid |
| 56) | 5-methyl-3-(n-hexyloxycarbonylamino)salicylic acid |
| 57) | 5-cyclohexyl-3-(phenyloxycarbonylamino)salicylic acid |
| 58) | 5-cumyl-3-(n-hexyloxycarbonylamino)salicylic acid |
| 59) | 3-(n-octylthiolcarbonylamino)salicylic acid |
| 60) | 3-[(4'-chlorobenzyl)thiolcarbonylamino]salicylic acid |
| 61) | 3-[(3'-methylphenyl)thiolcarbonylamino]salicylic acid |
| 62) | 3-(n-butylthiolthiocarbonylamino)salicylic acid |
| 63) | 3-(phenylthiolthiocarbonylamino)salicylic acid |
| 64) | 3-[(4'-ethoxyphenyl)thiolthiocarbonylamino]salicylic acid |
| 65) | 3-(N-phenyl-N-phenyloxycarbonylamino)salicylic acid |
| 66) | 4-(methyloxycarbonylamino)salicylic acid |
| 67) | 4-(ethyloxycarbonylamino)salicylic acid |
| 68) | 4-(n-propyloxycarbonylamino)salicylic acid |
| 69) | 4-(isopropyloxycarbonylamino)salicylic acid |
| 70) | 4-(n-butyloxycarbonylamino)salicylic acid |
| 71) | 4-(isobutyloxycarbonylamino)salicylic acid |
| 72) | 4-(sec-butyloxycarbonylamino)salicylic acid |
| 73) | 4-(n-pentyloxycarbonylamino)salicylic acid |
| 74) | 4-(isopentyloxycarbonylamino)salicylic acid |
| 75) | 4-(n-hexyloxycarbonylamino)salicylic acid |
| 76) | 4-(n-heptyloxycarbonylamino)salicylic acid |
| 77) | 4-(n-octyloxycarbonylamino)salicylic acid |
| 78) | 4-[(2'-ethylhexyl)oxycarbonylamino]salicylic acid |
| 79) | 4-(n-nonyloxycarbonylamino)salicylic acid |
| 80) | 4-(n-decyloxycarbonylamino)salicylic acid |
| 81) | 4-(n-undecyloxycarbonylamino)salicylic acid |
| 82) | 4-(n-dodecyloxycarbonylamino)salicylic acid |
| 83) | 4-(n-tridecyloxycarbonylamino)salicylic acid |
| 84) | 4-(n-tetradecyloxycarbonylamino)salicylic acid |
| 85) | 4-(n-pentadecyloxycaronylamino)salicylic acid |
| 86) | 4-(n-hexadecyloxycarbonylamino)salicylic acid |
| 87) | 4-(n-heptadecyloxycarbonylamino)salicylic acid |
| 88) | 4-(n-octadecyloxycarbonylamino)salicylic acid |
| 89) | 4-(cyclopentyloxycarbonylamino)salicylic acid |
| 90) | 4-(cyclohexyloxycarbonylamino)salicylic acid |
| 91) | 4-[(4'-tert-butylcyclohexyl)oxycarbonylamino]salicylic acid |
| 92) | 4-(cycloheptyloxycarbonylamino)salicylic acid |
| 93) | 4-(cyclooctyloxycarbonylamino)salicylic acid |
| 94) | 4-(cyclohexylmethyloxycarbonylamino)salicylic acid |
| 95) | 4-[(2'-tetrahydrofurfuryl)oxycarbonylamino]salicylic acid |
| 96) | 4-[(2'-methoxyethyl)oxycarbonylamino]salicylic acid |
| 97) | 4-[(2'-n-hexyloxyethyl)oxycarbonylamino]salicylic acid |
| 98) | 4-[(2'-n-octyloxyethyl)oxycarbonylamino]salicylic acid |
| 99) | 4-[(3'-ethoxypropyl)oxycarbonylamino]salicylic acid |
| 100) | 4-[(3'-n-butoxypropyl)oxyaarbonylamino]salicylic acid |
| 101) | 4-[(3'-n-octyloxypropyl)oxycarbonylamino]salicylic acid |
| 102) | 4-[(2'-n-butoxyethoxyethyl)oxycarbonylamino]salicylic acid |
| 103) | 4-[(2'-benzyloxyethyl)oxycarbonylamino]salicylic acid |
| 104) | 4-[(phenoxymethyl)oxycarbonylamino]salicylic acid |
| 105) | 4-[(2'-phenoxyethyl)oxycarbonylamino]salicylic acid |
| 106) | 4-[2'-(4-chlorophenyl)oxyethyloxycarbonylamino]salicylic acid |
| 107) | 4-[2'-(4-methoxyphenyl)oxyethyloxycarbonylamino]salicylic acid |
| 108) | 4-[(2'-phenoxyethoxyethyl)oxycarbonylamino]salicylic acid |
| 109) | 4-[(3'-n-butylthiopropyl)oxycarbonylamino]salicylic acid |
| 110) | 4-[(6'-ethylthiohexyl)oxycarbonylamino]salicylic acid |
| 111) | 4-[(2'-benzylthioethyl)oxycarbonylamino]salicylic acid |
| 112) | 4-[(2'-phenylthioethyl)oxycarbonylamino]salicylic acid |
| 113) | 4-[(2'-chloroethyl)oxycarbonylamino]salicylic acid |
| 114) | 4-[(9'-decenyl)oxycarbonylamino]salicylic acid |
| 115) | 4-(benzyloxycarbonylamino)salicylic acid |
| 116) | 4-[(4'-methylbenzyl)oxycarbonylamino]salicylic acid |
| 117) | 4-[(4'-chlorobenzyl)oxycarbonylamino]salicylic acid |
| 118) | 4-[(2'-phenylethyl)oxycarbonylamino]salicylic acid |
| 119) | 4-(phenyloxycarbonylamino)salicylic acid |
| 120) | 4-[(1'-naphthyl)oxycarbonylamino]salicylic acid |
| 121) | 4-[(2'-naphthyl)oxycarbonylamino]salicylic acid |
| 122) | 4-[(2'-furyl)oxycarbonylamino]salicylic acid |
| 123) | 4-[(4'-phenylphenyl)oxycarbonylamino]l ]salicylic acid |
| 124) | 4-[(4'-methylphenyl)oxycarbonylamino]salicylic acid |
| 125) | 4-[(3'-methylphenyl)oxycarbonylamino]salicylic acid |
| 126) | 4-[(2'-methylphenyl)oxycarbonylamino]salicylic acid |
| 127) | 4-[(4'-ethylphenyl)oxycarbonylamino]salicylic acid |
| 128) | 4-[(4'-tert-butylphenyl)oxycarbonylamino]salicylic acid |
| 129) | 4-[(4'-cyclohexylphenyl)oxycarbonylamino]salicylic acid |
| 130) | 4-[(2'-cyclohexylphenyl)oxycarbonylamino]salicylic acid |
| 131) | 4-[(4'-cumylphenyl)oxycarbonylamino]salicylic acid |
| 132) | 4-[(4'-methoxyphenyl)oxycarbonylamino]salicylic acid |
| 133) | 4-[(3'-methoxyphenyl)oxycarbonylamino]salicylic acid |
| 134) | 4-[(2'-ethoxyphenyl)oxycarbonylamino]salicylic acid |
| 135) | 4-[(4'-n-butoxyphenyl)oxycarbonylamino]salicylic acid |
| 136) | 4-[(4'-n-hexyloxyphenyl)oxycarbonylamino]salicylic acid |
| 137) | 4-[(4'-benzyloxyphenyl)oxycarbonylamino]salicylic acid |
| 138) | 4-[4'-(4-benzyloxycumyl)phenyloxycarbonylamino]salicylic acid |
| 139 | 4-[(4'-phenoxyphenyl)oxycarbonylamino]salicylic acid |
| 140) | 4-[2'-(6-benzyloxy)naphthyloxycarbonylamino]salicylic acid |
| 141) | 4-[(4'-phenylcarbonylphenyl)oxycarbonylamino]salicylic acid |
| 142) | 4-[(4'-acetylphenyl)oxycarbonylamino]salicylic acid |
| 143) | 4-[(4'-ethoxycarbonylphenyl)oxycarbonylamino]salicylic acid |
| 144) | 4-[(4'-cyclohexyloxycarbonylphenyl)oxycarbonylamino] salicylic acid |
| 145) | 4-[(4'-n-propylcarbonyloxyphenyl)oxycarbonylamino]salicylic acid |
| 146) | 4-[(4'-n-methylthiophenyl)oxycarbonylamino]salicylic acid |

| No. | Compound |
|---|---|
| 147) | 4-[(4'-benzylthiophenyl)oxycarbonylamino]salicylic acid |
| 148) | 48)4-[(4'-fluorophenyl)oxycarbonylamino]salicylic acid |
| 149) | 4-[(2'-fluorophenyl)oxycarbonylamino]salicylic acid |
| 150) | 4-[(4'-chlorophenyl)oxycarbonylamir<salicylic acid |
| 151) | 4-[(3'-chlorophenyl)oxycarbonylamino]salicylic acid |
| 152) | 4-[(4'-bromophenyl)oxycarbonylamino]salicylic acid |
| 153) | 4-[(4'-nitrophenyl)oxycarbonylamino]salicylic acid |
| 154) | 4-[(4'-formylphenyl)oxycarbonylamino]salicylic acid |
| 155) | 4-[(4'-cyanophenyl)oxycarbonylamino]salicylic acid |
| 156) | 4-[(2',4'-dimethylphenyl)oxycarbonylamino]salicylic acid |
| 157) | 4-[(3',5'-dimethylphenyl)oxycarbonylamino]salicylic acid |
| 158) | 4-[(2',4'-dichlorophenyl)oxycarbonylamino]salicylic acid |
| 159) | 4-[(3',5'-dimethoxyphenyl)oxycarbonylamino]salicylic acid |
| 160) | 4-[(3'-nitro-4'-chlorophenyl)oxycarbonylamino]salicylic acid |
| 161) | 4-[(4'-chloro-2'-methylphenyl)oxycarbonylamino]salicylic acid |
| 162) | 4-(n-octylthiolcarbonylamino)salicylic acid |
| 163) | 4-(phenylthiolcarbonylamino)salicylic acid |
| 164) | 4-[(4'-ethoxyphenylthiol)carbonylamino]salicylic acid |
| 165) | 4-(n-hexylthiolthiocarbonylamino)salicylic acid |
| 166) | 4-[(4'-methylphenylthiol)thiocarbonylamino]salicylic acid |
| 167) | 4-(n-decyloxythiocarbonylamino)salicylic acid |
| 168) | 4-(N-n-butyl-N-heptyloxycarbonylamino)salicylic acid |
| 169) | 3-ethyl-4-(phenyloxycarbonylamino)salicylic acid |
| 170) | 3-chloro-4-(n-butyloxycarbonylamino)salicylic acid |
| 171) | 5-(methyloxycarbonylamino)salicylic acid |
| 172) | 5-(ethyloxycarbonylamino)salicylic acid |
| 173) | 5-(n-propyloxycarbonylamino)salicylic acid |
| 174) | 5-(n-butyloxycarbonylamino)salicylic acid |
| 175) | 5-(isobutyloxycarbonylamino)salicylic acid |
| 176) | 5-(n-pentyloxycarbonylamino)salicylic acid |
| 177) | 5-(isopentyloxycarbonylamino)salicylic acid |
| 178) | 5-(n-hexyloxycarbonylamino)salicylic acid |
| 179) | 5-(n-heptyloxycarbonylamino)salicylic acid |
| 180) | 5-(n-octyloxycarbonylamino)salicylic acid |
| 181) | 5-[(2'-ethylhexyl)oxycarbonylamino]salicylic acid |
| 182) | 5-(n-nonyloxycarbonylamino)salicylic acid |
| 183) | 5-(n-decyloxycarbonylamino)salicylic acid |
| 184) | 5-(n-undecyloxycarbonylamino)salicylic acid |
| 185) | 5-(n-dodecyloxycarbonylamino)salicylic acid |
| 186) | 5-(n-tetradecyloxycarbonylamino)salicylic acid |
| 187) | 5-(n-hexadecyloxycarbonylamino)salicylic acid |
| 188) | 5-(cyclohexyloxycarbonylamino)salicylic acid |
| 189) | 5-[(4'-methylcyclohexyl)Oxycarbonylamino]salicylic acid |
| 190) | 5-[(4'-tert-butylcyclohexyl)oxycarbonylamino]salicylic acid |
| 191) | 5-[(2'-cyclohexylethyl)oxycarbonylamino]salicylic acid |
| 192) | 5-(cyclooctyloxycarbonylamino)salicylic acid |
| 193) | 5-[(2'-tetrahydrofurfuryl)oxycarbonylamino]salicylic acid |
| 194) | 5-[(2'-methoxyethyl)oxycarbonylamino]salicylic acid |
| 195) | 5-[(2'-n-hexyloxyethyl)oxycarbonylamino]salicylic acid |
| 196) | 5-[(3'-ethoxypropyl)oxycarbonylamino]salicylic acid |
| 197) | 5-[(3'-isopropoxypropyl)oxycarbonylamino]salicylic acid |
| 198) | 5-[(2'-methoxyethoxyethyl)oxycarbonylamino]salicylic acid |
| 199) | 5-(phenoxymethyloxycarbonylamino)salicylic acid |
| 200) | 5-(2'-phenoxyethyloxycarbonylamino)salicylic acid |
| 201) | 5-[2'-(4-chlorophenyl)oxyethyloxycarbonylamino]salicylic acid |
| 202) | 5-[2'-(4-methoxyphenyl)oxyethyloxycarbonylamino]salicylic acid |
| 203) | 5-[(2'-phenoxyethoxyethyl)oxycarbonylamino]salicylic acid |
| 204) | 5-[(2'-n-hexylthioethyl)oxycarbonylamino]salicylic acid |
| 205) | 5-[(2'-phenylthioethyl)oxycarbonylamino]salicylic acid |
| 206) | 5-(2'-chloroethyloxycarbonylamino)salicylic acid |
| 207) | 5-(5'-hexenyloxycarbonylamino)salicylic acid |
| 208) | 5-(benzyloxycarbonylamino)salicylic acid |
| 209) | 5-[(4'-methylbenzyl)oxycarbonylamino]salicylic acid |
| 210) | 5-[(4'-chlorobenzyl)oxycarbonylamino]salicylic acid |
| 211) | 5-[(2'-phenylethyl)oxycarbonylamino]salicylic acid |
| 212) | 5-(phenyloxycarbonylamino)salicylic acid |
| 213) | 5-[(2'-naphthyl)oxycarbonylamino]salicylic acid |
| 214) | 5-[(4'-phenylphenyl)oxycarbonylamino]salicylic acid |
| 215) | 5-[(3'-methylphenyl)oxycarbonylamino]salicylic acid |
| 216) | 5-[(4'-ethylphenyloxycarbonylamino]]salicylic acid |
| 217) | 5-[(4'-cyclohexylphenyl)oxycarbonylamino]salicylic acid |
| 218) | 5-[(4'-cumylphenyl)oxycarbonylamino]salicylic acid |
| 219) | 5-[(4'-methoxyphenyl)oxycarbonylamino]salicylic acid |
| 220) | 5-[(3'-ethoxyphenyl)oxycarbonylamino]salicylic acid |
| 221) | 5-[(4'-n-butoxyphenyl)oxycarbonylamino]salicylic acid |
| 222) | 5-[(4'-phenoxyphenyl)oxycarbonylamino]salicylic acid |
| 223) | 5-[(4'-acetylphenyl)oxycarbonylamino]salicylic acid |
| 224) | 5-[(4'-methoxycarbonylphenyl)oxycarbonylamino]salicylic acid |
| 225) | 5-[(4'-ethylcarbonyloxyphenyl)oxycarbonylamino]salicylic acid |
| 226) | 5-[(4'-ethylthiophenyl)oxycarbonylamino]salicylic acid |
| 227) | 5-[(4'-phenylthiophenyl)oxycarbonylamino]salicylic acid |
| 228) | 5-[(4'-fluorophenyl)oxycarbonylamino]salicylic acid |
| 229) | 5-[(3'-fluorophenyl)oxycarbonylamino]salicylic acid |
| 230) | 5-[(4'-chlorophenyl)oxycarbonylamino]salicylic acid |
| 231) | 5-[(3'-chlorophenyl)oxycarbonylamino]salicylic acid |
| 232) | 5-[(2'-chlorophenyl)oxycarbonylamino]salicylic acid |
| 233) | 5-[(2'-formylphenyl)oxycarbonylamino]salicylic acid |
| 234) | 5-[(2'-cyanophenyl)oxycarbonylamino]salicylic acid |
| 235) | 5-[(2',4'-dimethylphenyl)oxycarbonylamino]salicylic acid |
| 236) | 5-[(3',5'-dimethylphenyl)oxycarbonylamino]salicylic acid |
| 237) | 5-[(3'-nitro-4'-chlorophenyl)oxycarbonylamino]salicylic acid |
| 238) | 5-(n-butylthiolcarbonylamino)salicylic acid |
| 239) | 5-(phenylthiolcarbonylamino)salicylic acid |
| 240) | 5-[(2'-naphthylthiol)carbonylamino]salicylic acid |
| 241) | 5-[(4'-methylphenylthiol)carbonylamino]salicylic acid |
| 242) | 5-(n-heptylthiolthiocarbonylamino)salicylic acid |
| 243) | 5-(n-dodecylthiolthiocarbonylamino)salicylic acid |
| 244) | 5-(n-pentyloxythiocarbonylamino)salicylic acid |
| 245) | 5-[(4'-chlorophenyl)oxythiocarbonylamino]salicylic acid |
| 246) | 5-(N-methyl-N-phenyloxycarbonylamino)salicylic acid |
| 247) | 3-methyl-5-(methyloxycarbonylamino)salicylic acid |
| 248) | 3-ethoxy-5-(n-butyloxycarbonylamino)salicylic acid |
| 249) | 3-c-methylbenzyl-5-(ethyloxycarbonylamino)salicylic acid |
| 250) | 3-phenyl-5-(n-hexyloxycarbonylamino)salicylic acid |
| 251) | 6-(n-propyloxycarbonylamino)salicylic acid |
| 252) | 6-(isopentyloxycarbonylamino)salicylic acid |
| 253) | 6-(n-heptyloxycarbonylamino)salicylic acid |
| 254) | 6-[(1'-methylheptyl)oxycarbonylamino]salicylic acid |
| 255) | 6-(n-dodecyloxycarbonylamino)salicylic acid |
| 256) | 6-[(2',5'-dimethylcyclohexyl)oxycarbonylamino]salicylic acid |
| 257) | 6-[(2'-cyclohexylmethyl)oxycarbonylamino]salicylic acid |
| 258) | 6-[(3'-butenyl)oxycarbonylamino]salicylic acid |
| 259) | 6-[(10'-undecenyl)oxycarbonylamino]salicylic acid |
| 260) | 6-[(2'-isopropoxyethyl)oxycarbonylamino]salicylic acid |
| 261) | 6-[(3'-cyclohexyloxypropyl)oxycarbonylamino]salicylic acid |
| 262) | 6-[(2'-phenethyloxyethyl)oxycarbonylamino]salicylic acid |
| 263) | 6-[(2'-phenoxyethyl)oxycarbonylamino]salicylic acid |
| 264) | 6-[(2'-(4-chlorophenoxy)ethyloxycarbonylamino]salicylic acid |
| 265) | 6-[(3'-n-buthylthiopropyl)oxycarbonylamino]salicylic acid |
| 266) | 6-[(3'-(4-methylbenzylthio)propyloxycarbonylamino]salicylic acid |
| 267) | 6-[(2'-phenylthioethyl)oxycarbonylamino]salicylic acid |
| 268) | 6-[(2'-tetrahydrofurfuryl)oxycarbonylamino]salicylic acid |
| 269) | 6-[(2'-chloroethyl)oxycarbonylamino]salicylic acid |
| 270) | 6-(benzyloxycarbonylamino)salicylic acid |
| 271) | 6-[(4'-chlorobenzyl)oxycarbonylamino]salicylic acid |
| 272) | 6-(phenyloxycarbonylamino)salicylic acid |
| 273) | 6-[(1'-naphthyl)oxycarbonylamino]salicylic acid |
| 274) | 6-[(4'-phenylphenyl)oxycarbonylamino]salicylic acid |
| 275) | 6-[(2'-ethylphenyl)oxycarbonylamino]salicylic acid |
| 276) | 6-[(4'-tert-butylphenyl)oxycarbonylamino]salicylic acid |
| 277) | 6-[(3'-methoxyphenyl)oxycarbonylamino]l]salcylic acid |
| 278) | 6-[(4'-n-hexyloxyphenyl)oxycarbonylamino]salicylic acid |
| 279) | 6-[(3'-phenoxyphenyl)oxycarbonylamino]salicylic acid |
| 280) | 6-[(4'-ethylcarbonylphenyl)oxycarbonylamino]salicylic acid |
| 281) | 6-[(4'-benzylcarbonylphenyl)oxycarbonylamino]salicylic acid |
| 282) | 6-[(4'-methoxycarbonylphenyl)oxycarbonylamino]salicylic acid |
| 283) | 6-[(4'-methylthiophenyl)oxycarbonylamino]salicylic acid |
| 284) | 6-[(3'-fluorophenyl)oxycarbonylamino]salicylic acid |
| 285) | 6-[(2'-chlorophenyl)oxycarbonylamino]salicylic acid |
| 286) | 6-[(3'-nitrophenyl)oxycarbonylamino]salicylic acid |
| 287) | 6-[(2'-formylphenyl)oxycarbonylamino]salicylic acid |
| 288) | 6-[(3'-hydroxyphenyl)oxycarbonylamino]salicylic acid |
| 289) | 6-[(4'-cyanophenyl)oxycarbonylamino]salicylic acid |
| 290) | 6-[(3',4'-dimethylphenyl)oxycarbonylamino]salicylic acid |
| 291) | 6-[(2',4'-dichlorophenyl)oxycarbonylamino]salicylic acid |
| 292) | 3-ethyl-6-(n-hexyloxycarbonylamino)salicylic acid |
| 293) | 3-tert-butyl-6-(phenyloxycarbonylamino)salicylic acid |
| 294) | 6-(N-ethyl-N-phenyloxycarbonylamino)salicylic acid |
| 295) | 6-(n-octylthiolcarbonylamino)salicylic acid |
| 296) | 6-[(4'-methylbenzyl)thiolcarbonylamino]salicylic acid |
| 297) | 6-[(4'-methylphenyl)thiolcarbonylamino]salicylic acid |
| 298) | 6-(n-octylthiolthiocarbonylamino)salicylic acid |
| 299) | 6-(phenylthiolthiocarbonylamino)salicylic acid |

| No. | Compound |
|---|---|
| 300) | 6-[(4'-methoxyphenyl)thiolthiocarbonylamino]salicylic acid |

The metal salts of the salicylic acid derivatives represented by the formula(1) which is used for the electron accepting compound in the heat-sensitive recording material of the invention include salts of monovalent metals such as sodium, potassium and lithium and polyvalent metals having 2, 3 and 4 valence. In the case of using the metal salt singly as an electron accepting compound, the salt is preferably a metal salt which is difficultly soluble or insoluble in water and composed of a polyvalent metal of 2, 3 and 4 valence, more preferably a salt of the polyvalent metal having 2 or 3 valence.

Exemplary metal salts are salts of sodium, potassium, lithium, zinc, cadmium, mercury, magnesium, calcium, barium, nickel, tin, gallium, chromium, copper, molybdenum, wolfram, zirconium, strontium, manganese, cobalt, titanium, aluminum and iron, preferably salts of zinc, calcium, barium, nickel, manganese, cobalt and aluminum, more preferably salts of zinc, magnesium, nickel and manganese, most preferably a zinc salt.

The metal salt of the salicylic acid derivative can be used for the heat-sensitive recording material of the invention. The salicylic acid derivative represented by the formula(1) and the metal salt of the derivative can be used singly or as a mixture for the electron accepting compound in the heat-sensitive recording material of the invention. For example, a combination of one or more salicylic acid derivatives and a metal salt of salicylic acid derivative can also be used.

The salicylic acid derivative represented by the formula (1) or the metal salt of the derivative which is used in the invention can be prepared by known processes described, for example, in J. Pharm. Sci., 52,927(1963) and Bull.de. Socie. Chim. France, 1189(1955). That is, the derivative and its metal salt can be suitably prepared, for example, by reacting an aminosalicylic acid derivative with an almost equivalent amount of a chloroformate compound.

The heat-sensitive recording material of the invention is characterized in that the preferred preservation characteristic of developed images, good preservation stability of white portions and very excellent thermal response can be obtained by using the aliphatic amide compound described below in combination with the above salicylic acid derivative or the metal salt of the derivative.

The aliphatic amide compound that can be used in the invention and has 18~60 carbon atoms in the molecular structure is represented by the formula (3):

$$R_3CONH_2 \quad (3)$$

wherein $R_3$ is an alkyl group or an alkenyl group and has 17~59 carbon, the formula (4):

$$R_4CONHR_5 \quad (4)$$

wherein $R_4$ is an alkyl group or an alkenyl group, $R_5$ is an alkyl group, an alkenyl group or a hydroxymethyl group, and the sum of carbon atoms in $R_4$ and $R_6$ is 17~59, the formula (5):

$$R_6CONHR_7NHOCH_6 \quad (5)$$

wherein $R_4$ is an alkyl group or an alkenyl group, $R_7$ is a divalent aliphatic radical and the sum of carbon atoms in $R_6$ and $R_7$ is 16~58. or the formula (6):

$$R_8NHOCR_9CONHR_8 \quad (6)$$

wherein $R_8$ is an alkyl group or an alkenyl group, $R_9$ is a divalent aliphatic group, and the sum of carbon atoms in $R_8$ and $R_9$ is 16~58.

Exemplary compounds represented by the formula (3) include stearic acid amide, oleic acid amide, behenic acid amide, erucic acid amide, tricosanoic acid amide, lignoceric acid amide, pentacosanoic acid amide, cerotic acid amide and melissic acid amide.

Exemplary compounds represented by the formula (4) include: N-octylpalmitic acid amide, N-methylstearic acid amide, N-ethylstearic acid amide, N-butylstearic acid amide, N-cyclohexylstearic acid amide, N-decylstearic acid amide, N-stearylstearic acid amide, N-oleylstearic acid amide, N-hydroxyymethylstearic acid amide and N-hydroxymethylbehen ic acid amide.

Exemplary compounds represented by the formula (5) include: ethylenebisstearic acid amide, butylenebisstearic acid amide, pentamethylenebisstearic acid amide, hexamethylenebisoleic acid amide. hexamethylenebisstearic acid amide, hexamethylenebislauric acid amide, hexamethylenebispalmitic acid amide, and octamethylenebispalmitic acid amide.

Exemplary compounds represented by the formula (6) include

N,N'-dihexylsebacic acid amide,
N,N'-dioctyladipic acid amide,
N,N'-dilauryladipic acid amide,
N,N'-dipalmityladipic acid amide,
N,N'-distearylpimelic acid amide,
N,N'-distearylsuberic acid amide,
N,N'-distearylazelaic acid amide,
N,N'-dioleyladipic acid amide,
N,N'-dioleylsebacic acid amide,
N,N'-distearyladipic acid amide, and
N,N'-distearylsebacic acid amide.

These aliphatic amide compounds can be used singly or as a mixture.

When the aliphatic amide compound having 18~60 carbon atoms in the molecular structure is used in combination with an electron accepting compound, that is, the salicylic acid derivative represented by the formula (1) or the metal salt of the derivative, thermal response of the heat-sensitive recording material can be improved without giving an adverse effect on the preservation stability of white portions and images.

When an aliphatic amide compound having 19 or more carbon atoms is used, wet heat resistance (i.e. resistance to heat under a moist environment), which is an attribute of the image preservation stability, is improved as compared with when an aliphatic amide having 18 carbon atoms is used. That is, the aliphatic amide compound has preferably 19~60 carbon atoms, more preferably 19~50 carbon atoms in the molecular structure. Use of such aliphatic amide compound in combination provides a heat-sensitive recording material which is excellent in preservation stability of white portions and images, and particularly excellent in thermal response.

When the aliphatic amide compound has less than 18 carbon atoms in the molecular structure, the resulting heat-sensitive recording material is inferior in preservation stability of white portions, particularly in heat resistance, and additionally its sensitivity for color development is insufficiently improved. On the other hand, the aliphatic amide compound having more than 60 carbon atoms in the molecular structure renders inferior preservation stability for the heat-sensitive recording material and is unfavorably difficult to obtain in some cases. The amount of the aliphatic amide compound is preferably 10~300% by weight, more preferably 20~200% by weight based on the salicylic acid derivative of the formula (1) or the metal salt of the derivative.

In the heat-sensitive recording material of the invention, a usually colorless or pale colored dyestuff precursor having electron donating ability and an electron accepting compound are generally used as principal components, these components are dispersed in a binder and coated on a substrate to form a heat-sensitive recording layer, and the layer is heated by a thermal head, hot pen or laser beam to develop recording images by an instantaneous reaction between the dyestuff precursor and the electron accepting compound. The process has been disclosed in Japanese Patent Publication SHO 43-4160 and 45-14039.

Fillers, sensitizers, antioxidants and antisticking agents are added to the heat-sensitive recording layer, when desired.

No particular restriction is imposed upon the dyestuff precursor for use in the heat-sensitive recording material of the invention as long as the dyestuff precursor is generally used for pressure-sensitive recording or heat-sensitive recording.

Practical electron donating compounds will be illustrated below.

(1) The triarylmethane compounds include, for example, 3,3-bis(4-dimethylaminophenyl)-6-dimethylaminophthalide [crystal violet lactone],
3,3-bis(4-dimethylaminophenyl)phthalide,
3-(4-dimethylaminophenyl)-3-(1,3-dimethylindol-3-yl)phthalide,
3-(4-dimethylaminophenyl)-3-(2-methylindol-3-yl)phthalide,
3,3-bis(9-ethylcarbazole-3-yl)-6-dimethylaminophthalide,
3-(4-dimethylaminophenyl)-3-(1-methylpyrrol-3-yl)-6-dimethylaminophthalide, and
3,3-bis[2,2-bis(4-dimethylaminophenyl)ethenyl-4,5,6,7-tetrachlorophthalide.

(2) Diarylmethane compounds include, for example,
4,4-bis-dimethylaminobenzhydrin benzyl ether, N-halophenylleucoauramine, and
N-2,4,5-trichlorophenylleucoauramine.

(3) Rhodamine-lactam compounds include, for example, rhodamine-B-anilinolactam, rhodamine-(4-nitroanilino)lactam, and
rhodamine-B-(4-chloroanilino)lactam.

(4) Fluoran compounds include, for example, 3,6-dimethoxyfluoran, 3-dimethylamino-7-methoxyfluoran,
3-diethylamino-6-methoxyfluoran, 3-diethylamino-7-methoxyfluoran,
3-diethylamino-7-chlorofluoran,
3-diethylamino-6-methyl-7-chlorofluoran
3-diethylamino-6,7-dimethylfluoran,
3-N-cyclohexyl-N-n-butylamino-7-methylfluoran,
3-diethylamino-7-dibenzylaminofluoran,
3-diethylamino-7-octylaminofluoran,
3-diethylamino-7-di-n-hexylaminofluoran,
3-diethylamino-7-anilinofluoran,
3-diethylamino-7-(2-chloroanilino)fluoran,
3-diethylamino-7-(3-chloroanilino)fluoran,
3-diethylamino-7-(2,3-dichloroanilino)fluoran,
3-diethylamino-7-(3-trifluoromethylanilino)fluoran,
3-di-n-butylamino-7-(2-chloroanilino)fluoran,
3-diethylamino-6-chloro-7-anilinofluoran,
3-di-n-butylamino-6-chloro-7-anilinofluoran,
3-diethylamino-6-methoxy-7-anilinofluoran,
3-di-n-butylamino-6-ethoxy-7-anilinofluoran,
3-pyrrolidino-6-methyl-7-anilinofluoran,
3-morpholino-6-methyl-7-anilinofluoran,
3-dimethylamino-6-methyl-7-anilinofluoran,
3-diethylamino-6-methyl-7-anilinofluoran,
3-di-n-butylamino-6-methyl-7-anilinofluoran,
3-di-n-pentylamino-6-methyl-7-anilinofluoran,
3-di-n-octylamino-6-methyl-7-anilinofluoran,
3-N-ethyl-N-methylamino-6-methyl-7-anilinofluoran,
3-N-n-propyl-N-methylamino-6-methyl-7-anilinofluoran,
3-N-n-propyl-N-ethylamino-6-methyl-7-anilinofluoran,
3-N-isopropyl-N-methylamino-6-methyl-7-anilinofluoran,
3-N-n-butyl-N-methylamino-6-methyl-7-anilinofluoran,
3-N-n-butyl-N-ethylamino-6-methyl-7-anilinofluoran,
3-N-n-butyl-N-n-propylamino-6-methyl-7-anilinofluoran,
3-N-isobutyl-N-methylamino-6-methyl-7-anilinofluoran,
3-N-isobutyl-N-ethylamino-6-methyl-7-anilinofluoran,
3-N-isopentyl-N-ethylamino-6-methyl-7-anilinofluoran,
3-N-n-hexyl-N-ethylamino-6-methyl-7-anilinofluoran,
3-N-n-octyl-N-ethylamino-6-methyl-7-anilinofluoran,
3-N-cyclohexyl-N-methylamino-6-methyl-7-anilinofluoran,
3-N-cyclohexyl-N-n-propylamino-6-methyl-7-anilinofluoran,
3-N-cyclohexyl-N-n-butylamino-6-methyl-7-anilinofluoran,
3-N-cyclohexyl-N-n-pentylamino-6-methyl-7-anilinofluoran,
3-N-cyclohexyl-N-n-hexylamino-6-methyl-7-anilinofluoran,
3-N-cyclohexyl-N-n-heptylamino-6-methyl-7-anilinofluoran,
3-N-cyclohexyl-N-n-octylamino-6-methyl-7-anilinofluoran,
3-N-cyclohexyl-N-n-decylamino-6-methyl-7-anilinofluoran,
3-N-2'-methoxyethyl-N-methylamino-6-methyl-7-anilinofluoran,
3-N-2'-methoxyethyl-N-ethylamino-6-methyl-7-anilinofluoran,
3-N-2'-methoxyethyl-N-isobutylamino-6-methyl-7-anilinofluoran,
3-N-2'-ethoxyethyl-N-methylamino-6-methyl-7-anilinofluoran,
3-N-2'-ethoxyethyl-N-ethylamino-6-methyl-7-anilinofluoran,
3-N-3'-methoxypropyl-N-methylamino-6-methyl-7-anilinofluoran, 3-N-3'-methoxypropyl-
-N-ethylamino-6-methyl-7-anilinofluoran,
3-N-3'-ethoxypropyl-N-methylamino-6-methyl-7-anilinofluoran,
3-N-3'-ethoxypropyl-N-ethylamino-6-methyl-7-anilinofluoran,
3-N-2'-tetrahydrofurfuryl-N-ethylamino-6-methyl-7-anilinofluoran,
3-N-(4'-methylphenyl)-N-ethylamino-6-methyl-7-anilinofluoran,
3-diethylamino-6-ethyl-7-anilinofluoran,
3-diethylamino-6-methyl-7-(3'-methylphenylamino)fluoran,
3-diethylamino-6-methyl-7-(2',6'-dimethylphenylamino)fluoran,
3-di-n-butylamino-6-methyl-7-(2',6'-dimethylphenylamino)fluoran,
3-di-n-butylamino-7-(2',6'-dimethylphenylamino)fluoran,
2,2-bis[4'-(3-N-cyclohexyl-N-methylamino-6-methylfluoran-7-ylaminophenyl]propane, and
3-[4'-(4-phenylaminophenyl)aminophenyl]amino-6-methyl-7-chlorofluoran.

(5) Indolylphthalide compounds include, for example, 3,3-bis(1-ethyl-2-methylindole-3-yl)phthalide,
3,3-bis(1-octyl-2-methylindole-3-yl)phthalide,
3-(2-ethoxy-4-diethylaminophenyl)-3-(1-ethyl-2-methylindole-3-yl)phthalide,
3-(2-ethoxy-4-dibutylaminophenyl)-3-(1-ethyl-2-methylindole-3-yl) phthalide, and
3-(2-ethoxy-4-diethylaminophenyl)-3-(1-octyl-2-methylindole-3-yl) phthalide.

(6) Pyridine compounds include, for example, 3-(2-ethoxy-4-diethylaminophenyl)-3-(1-octyl-2-methylindole-3-yl) -4 or 7-azaphthalide,
3-(2-ethoxy-4-diethylaminophenyl)-3-(1-ethyl-2-methylindole-3-yl) -4 or 7-azaphthalide,
3-(2-hexyloxy-4-diethylaminophenyl)-3-(1-ethyl-2-methylindole-3-yl) -4 or 7-azaphthalide,
3-(2-ethoxy-4-diethylaminophenyl)-3-(1-ethyl-2-phenylindole-3-yl) -4 or 7-azaphthalide, and
3-(2-butoxy-4-diethylaminophenyl)-3-(1-ethyl-2-phenylindole-3-yl) -4 or 7-azaphthalide.

(7) Spiro compounds include, for example, 3-methyl-spiro-dinaphthopyran, 3-ethyl-spiro-dinaphthopyran,
3-phenyl-spiro-dinaphthopyran, 3-benzyl-spiro-dinaphthopyran,
3-methyl-naphtho-(3-methoxybenzo)spiropyran, and
3-propyl-spiro-dibenzopyran.

(8) Fluorerie compounds include, for example,

3',6',-bis(diethylamino)-5-diethylaminospiro(isobenzofuran-1,9'-fluorene)-3-one, and
3',6',-bis(diethylamino)-7-diethylamino-2-methylspiro(1,3-benzoxazine4,9'-fluorene).

These color forming, electron donating compounds can be used singly, or as a mixture in order to control color tone of developed image or to obtain multi-colored heat-sensitive recording materials.

The heat-sensitive recording material of the invention comprises as the electron accepting compound one or more salicylic acid derivatives of the formula(1) and/or the metal salts of said derivatives. Other electron accepting compounds can be simultaneously used in the range giving no adverse effect on the desired properties of the heat-sensitive recording material of the invention.

No particular restriction is imposed on the electron accepting compound to be used in combination with the salicylic acid derivative of the invention as long as the compound is an acidic substance and is generally used for heat-sensitive recording materials. For example, phenol derivatives, aromatic carboxylic acid derivatives, N,N'-diarylthiourea derivatives, and zinc salt and other multivalent metal salts of organic compounds can be used.

Practical examples of particularly preferred phenol derivatives include phenol compounds such as p-phenyphenol, p-hydroxyacetophenone, 4-hydroxy-4'-methyldiphenyl sulfone, 4-hydroxy-4'-isopropoxydiphenyl sulfone, 4-hydroxy-4'-benzenesulfonyloxydiphenyl sulfone, 1,1-bis(p-hydroxyphenyl)propane, 1,1-bis(p-hydroxyphenyl)pentane, 1,1-bis(p-hydroxyphenyl)hexane, 1,1-bis(p-hydroxyphenyl)cyclohexane, 2,2-bis(p-hydroxyphenyl)propane, 2,2-bis(p-hydroxyphenyl)hexane, 1,1-bis(p-hydroxyphenyl)-2-ethylhexane, 2,2-bis(3-chloro-4-hydroxyphenyl)propane, 1,1-bis(p-hydroxyphenyl)-1-phenylethane, 1,3-di-[2-(p-hydroxyphenyl)-2-propyl]benzene, 1,3-di-[2-(3,4-dihydroxydiphenyl)-2-propyl]benzene, 1,4-di-[2-(p-hydroxyphenyl)-2-propyl]benzene, 4,4'-dihydroxydiphenyl ether, 4,4'-dihydroxydiphenyl sulfone, 3,3'-dichloro-4,4'-dihydroxydiphenyl sulfone, 3,3'-diallyl-4,4'-dihydroxydiphenyl sulfone, 3,3'-dichloro-4,4'-dihydroxydiphenyl sulfide, methyl-2,2-bis(4'-hydroxyphenyl)acetate, n-butyl-4,4-(4'-hydroxyphenyl)acetate, 4,4'-thiobis(2-t-butyl-5-methylphenol), benzyl-p-hydroxybenzoate, chlorobenzyl-p-hydroxybenzoate, dimethyl-4-hydroxyphthalate, benzyl gallate, stearyl gallate, salicylic anilide, 5-chlorosalicylic anilide, salicylic acid, 3,5-di-tert-butylsalicylic acid, 3,5-di-α-methylbenzylsalicylic acid, 4-[2'-(4-methoxyphenyloxy) ethyloxy]salicylic acid, and metal salts.

Exemplary binders which can be used for the heat-sensitive recording material of the invention include water soluble adhesives such as starches, hydroxyethylcellulose, methylcellulose, gelatin, casein, polyvinyl alcohol, modified polyvinyl alcohol, sodium polyacrylate, and alkali metal salt of acrylic amide/acrylic ester copolymer, acrylic amide/acrylic ester/methacrylic acid ternary copolymer, styrene/maleic anhydride copolymer and ethylene/maleic anhydride copolymer; and latexes such as polyvinyl acetate, polyurethane, polyacrylic ester, styrene/butadiene copolymer, acrylonitrile/butadiene copolymer, methyl acrylate/butadiene copolymer and ethylene/vinyl acetate copolymer.

Fillers which can be used include, for example, diatomaceous earth, talc, kaolin, calcined kaolin, calcium carbonate, magnesium carbonate, titanium oxide, zinc oxide, silicon oxide, aluminum hydroxide and urea-formaldehyde resin.

Metal salts of higher fatty acids such as zinc stearate and calcium stearate, and waxes such as paraffin, oxidized paraffin, polyethylene, oxidized polyethylene, stearic acid amide and castor wax can be added in order to prevent head abrasion and sticking. Dispersants such as sodium dioctylsulfosuccinate, benzophenone base and benzotriazol base ultraviolet absorbers, surface active agents and fluorescent dyes can also be added, if desired.

The substrate used for the invention is primarily paper. Non-woven fabrics, plastic films, synthetic paper, metal foil or composite sheets obtained by combination of these matters can also be arbitrarily used. Further, application of an overcoat layer for protecting the heat-sensitive recording layer, application of single or more undercoat layers comprising fillers or resin between the heat-sensitive recording layer and the substrate, and a variety of other known techniques in the preparation of heat-sensitive recording materials can also be used in the invention.

The coating amount of the heat-sensitive recording layer depends upon the amounts of the dyestuff precursor and the electron accepting compound which are color developing components. The preferred amount of the dyestuff precursor is usually 0.1~1.0 g/m$^2$. The amount of the electron accepting compound is 5~700% by weight, preferably 20~500% by weight based on the dyestuff precursor.

Next, the present invention will be illustrated further in detail by way of examples. Part and percent in these examples are weight bases.

EXAMPLE 1

(A) Preparation of Heat-sensitive Coating Liquid

In a ball mill, 35 parts of dyestuff precursor 3-dibutylamino-6-methyl-7-anilinofluoran was ground for 24 hours with 80 parts of a 2.5% aqueous polyvinyl alcohol solution to obtain a dyestuff dispersion. Separately, 40 parts of zinc 4-n-octyloxycarbonylaminosalicylate, 60 parts of stearoyl acid amide and 300 parts of a 2.5% aqueous polyvinyl alcohol solution were ground in a sand mill (Trade Mark: DYNOMILL, manufactured by WEB Co.) to obtain a dispersion of the electron accepting compound having a volume average particle size of 2 μm or less. The above two dispersions were mixed.

The following ingredients were added to the mixture with stirring and thoroughly mixed to obtain heat-sensitive coating liquid.

| | |
|---|---|
| 30% Dyestuff dispersion | 115 parts |
| 25% Electron accepting compound dispersion | 400 parts |
| 50% Aqueous calcium carbonate dispersion | 100 parts |
| 40% Aqueous zinc stearate dispersion | 25 parts |
| 10% Aqueous polyvinyl alcohol solution | 200 parts |
| Water | 280 parts |

(B) Preparation of paper to be used for heat-sensitive coating

A coating liquid having the formulation described below was applied on a base paper having a basis weight of 40 g/m$^2$ so as to obtain a solid coating weight of 9 g/m$^2$, and dried to obtain the paper to be used for heat-sensitive coating.

| | |
|---|---|
| Calcined Kaolin | 100 parts |
| 50% Aqueous styrene/butadiene latex | 24 parts |
| Water | 200 parts |

(C) Preparation of heat-sensitive recording material

The heat-sensitive coating liquid prepared in (A) was coated on the paper prepared in (B) so as to obtain a solid coating weight of 4 g/m$^2$, and dried to obtain a heat-sensitive recording material.

(D) Evaluation of the heat-sensitive recording material

The heat-sensitive recording material thus prepared was calendered so as to obtain 400~500 seconds in Beck smoothness of the heat-sensitive surface, and successively following evaluation tests were carried out. Results are summarized in Table 1.

(1) Color Developing Property (Heat response)

Evaluation was carried out with a color developing test.

Color Developing Test

A printing test was carried out using a facsimile tester TH-PMD (Trade Mark of Ohkura Electric Co.). A thermal head having a dot density of 8 dots/mmhead resistance of 185Ω was used. Printing was carried out at a head voltage of 12V and pulse duration of 0.7 and 1.0 millisecond. Developed color density was measured by a Macbeth Model RD-918 reflection densitometer.

When the developed color density is 0.90 and more under a pulse duration of 0.7 millisecond or 1.30 and more under a pulse duration of 1.0 millisecond in this test, the color developing property is determined good. Color density of less than these values indicates poor color developing property.

(2) Preservation Property of White Portions

Evaluation was carried out with a heat resistance test and marker withstandability test.

Heat Resistance Test of White Portions

To test heat resistance, each sample specimen of the heat-sensitive recording material was allowed to stand at 60° C. for 24 hours, thereafter whiteness of each sample specimen was measured by a Macbeth Model RD-918 reflection densitometer. The higher the value, the higher cooling—i.e. poorer heat resistance.

When the whiteness after the heat treatment is 0.20 or less, the heat resistance is determined good; when the value exceeds 0.20, the property determined poor reflecting degraded image quality that likely to occur on use depending on printing conditions or smudging of white background during storing.

Marker Withstandability of White Background

To test the marker withstandability, a mark was put, using a fluorescent maker, on the non-imaged portion of the specimen sheet, which in turn was allowed to stand for 72 hours under a room temperature. Thereafter, the unmarked portion was inspected visually and the results were reported as follows;

◯: Substantially no smudging due to color development.

X: Appreciably smudging due to color development.

(3) Preservation Property of Images

Evaluation was carried out on three different scopes described as follows:

Wrapping Withstandability Test

A commercially available wrapping film was laid on each sample specimen that had been printed at 1.0 millisecond pulse duration and used in the aforesaid color development test. A weight rendering 2 g/cm$^2$ pressure is put on the wrapping film, and each of the thus wrapped and weight-loaded specimen sheet was allowed to stand for 24 hours at 40° C. Therafter, fading degree of the image was visually inspected, and the results were reported as follows;

: Image preserved, i.e. substantially no fading.
X: Image faded substantially, i.e. hardly legible.

Marker Withstandability Test

On each sample specimen that had been printed at 1.0 millisecond pulse duration and used in the color development test, a mark was put on the printed portion using a fluorescent marker. Each of the thus marked sample specimens was allowed to stand for 72 hours at room temperature. Thereafter, fading degree of the image was visually inspected, and the results were reported as follows;

: Image preserved, i.e. substantially no fading.
X: Image faded substantially, i.e. hardly legible.

Wet Heat Resistance Test

Each sample specimen that had been printed at 1.0 millisecond pulse duration and used in the color development test was allowed to stand for 24 hors at 40° C. and under 90% RH (relative humidity).

The printed image does fade after having undergone this hot and moist environment. Image density of the color on each of the sample specimens, before and after this test, were measured by Mackbeth Model RD-918 reflection densitometer, and residual rate was calculated by the following equation;

$$\text{Residual rate (\%)} = \frac{\text{image density after the test}}{\text{image density before the test}} \times 100$$

Preservation stability is determined good when the residual rate is 70% or higher; preservation stability is determined excellent when the rate is 80% or higher.

EXAMPLE 2

A heat-sensitive recording material was prepared by carrying out the same procedures as described in Example 1 except that zinc 4-n-octyloxycarbonylaminosalicylate was replaced by zinc 4-n-decyloxycarbonylaminosalicylate.

The heat-sensitive recording material obtained was evaluated by the same procedures as Example 1.

EXAMPLE 3

A heat-sensitive recording material was prepared by carrying out the same procedures as described in Example 1 except that zinc 4-n-octyloxycarbonylaminosalicylate was replaced by zinc 4phenyloxycarbonylaminosalicylate.

The heat-sensitive recording material obtained was evaluated by the same procedures as Example 1.

EXAMPLE 4

A heat-sensitive recording material was prepared by carrying out the same procedures as described in Example 1 except that stearic acid amide was replaced by behenic acid amide.

The heat-sensitive recording material obtained was evaluated by the same procedures as Example 1.

EXAMPLE 5

A heat-sensitive recording material was prepared by carrying out the same procedures as described in Example 1 except that stearic acid amide was replaced by N-hydroxymethylstearic acid amide.

The heat-sensitive recording material obtained was evaluated by the same procedures as Example 1.

EXAMPLE 6

A heat-sensitive recording material was prepared by carrying out the same procedures as described in Example 1 except that stearic acid amide was replaced by N-hydroxymethylbehenicacid amide.

The heat-sensitive recording material obtained was evaluated by the same procedures as Example 1.

EXAMPLE 7

A heat-sensitive recording material was prepared by carrying out the same procedures as described in Example 1 except that stearic acid amide was replaced by ethylenebisstearic acid amide.

The heat-sensitive recording material obtained was evaluated by the same procedures as Example 1.

EXAMPLE 8

A heat-sensitive recording material was prepared by carrying out the same procedures as described in Example 1 except that stearic acid amide was replaced by N-stearylstearic acid amide.

The heat-sensitive recording material obtained was evaluated by the same procedures as Example 1.

EXAMPLE 9

A heat-sensitive recording material was prepared by carrying out the same procedures as described in Example 1 except that stearic acid amide was replaced by N,N'-dioleylsebacic acid amide.

The heat-sensitive recording material obtained was evaluated by the same procedures as Example 1.

Comparative Example 1

A heat-sensitive recording material was prepared by carrying out the same procedures as described in Example 1 except that stearic acid amide was not used.

The heat-sensitive recording material obtained was evaluated by the same procedures as Example 1.

Comparative Example 2

A heat-sensitive recording material was prepared by carrying out the same procedures as described in Example 1 except that stearic acid amide was replaced by 2-benzyloxynaphthalene.

The heat-sensitive recording material obtained was evaluated by the same procedures as Example 1.

Comparative Example 3

A heat-sensitive recording material was prepared by carrying out the same procedures as described in Example 1 except that stearic acid amide was replaced by palmitic acid amide.

The heat-sensitive recording material obtained was evaluated by the same procedures as Example 1.

Comparative Example 4

A heat-sensitive recording material was prepared by carrying out the same procedures as described in Example 1 except that stearic acid amide was replaced by lauric acid amide.

The heat-sensitive recording material obtained was evaluated by the same procedures as Example 1.

Comparative Example 5

A heat-sensitive recording material was prepared by carrying out the same procedures as described in Example 1 except that zinc 4-n-octyloxycarbonylaminosalicylate was replaced by 2,2-bis(4-hydroxyphenyl)propane.

The heat-sensitive recording material obtained was evaluated by the same procedures as Example 1.

Comparative Example 6

A heat-sensitive recording material was prepared by carrying out the same procedures as described in Example 1 except that zinc 4-n-octyloxycarbonylaminosalicylate was replaced by zinc 3,5-bis(α-methylbenzyl)salicylate.

The heat-sensitive recording material obtained was evaluated by the same procedures as Example 1.

TABLE 1

| Example or Comparative Example | Color density 0.7 m sec | Color density 1.0 m sec | Preservation stability White portion Heat resistance | Preservation stability White portion Marker withstand- ability | Preservation stability Image Wrapping withstand- ability | Preservation stability Image Marker withstand- ability | Wet heat resistance (%) |
|---|---|---|---|---|---|---|---|
| Example 1 | 0.97 | 1.35 | 0.15 | ○ | ○ | ○ | 71 |
| Example 2 | 1.05 | 1.36 | 0.16 | ○ | ○ | ○ | 70 |
| Example 3 | 0.90 | 1.32 | 0.13 | ○ | ○ | ○ | 73 |
| Example 4 | 0.98 | 1.35 | 0.13 | ○ | ○ | ○ | 86 |
| Example 5 | 0.95 | 1.33 | 0.17 | ○ | ○ | ○ | 85 |
| Example 6 | 0.98 | 1.35 | 0.17 | ○ | ○ | ○ | 88 |
| Example 7 | 0.94 | 1.33 | 0.16 | ○ | ○ | ○ | 83 |
| Example 8 | 0.93 | 1.35 | 0.18 | ○ | ○ | ○ | 80 |
| Example 9 | 0.90 | 1.35 | 0.18 | ○ | ○ | ○ | 82 |
| Com. Example 1 | 0.56 | 1.12 | 0.12 | ○ | ○ | ○ | 85 |
| Com. Example 2 | 0.79 | 1.25 | 0.13 | ○ | ○ | ○ | 80 |
| Com. Example 3 | 0.93 | 1.35 | 0.46 | ○ | ○ | ○ | 65 |
| Com. Example 4 | 0.90 | 1.32 | 0.68 | ○ | ○ | ○ | 67 |
| Com. Example 5 | 1.10 | 1.35 | 0.15 | △ | X | X | 70 |
| Com. Example 6 | 1.06 | 1.32 | 0.65 | X | ○ | ○ | 72 |

What is claimed is:

1. A heat-sensitive recording material comprising a substrate having at least one layer thereon comprising:
   a colorless or pale colored dyestuff precursor;
   an electron accepting compound which develops the color of said dyestuff precursor by heat-reaction, wherein said electron accepting compound is one or more compounds selected from a salicylic acid derivative represented by the formula (1)

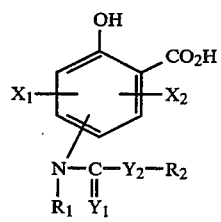
(1)

wherein $X_1$ and $X_2$ are a hydrogen atom, a halogen atom, an alkyl group, an alkoxy group, an aralkyl group or an aryl group, $Y_1$ and $Y_2$ are an oxygen atom or a sulfur atom, $R_1$ is a hydrogen atom, an alkyl group, an aralkyl group or an aryl group, and $R_2$ is an alkyl group, an alkenyl group, an aralkyl group or an aryl group, or a metal salt of said salicylic acid derivative, and
   an aliphatic amide compound having 18~60 carbon atoms.

2. The heat-sensitive recording material of claim 1 wherein the salicylic acid derivative represented by the formula (1) or the metal salt of said salicylic acid derivative is a salicylic acid derivative of the formula (2-c):

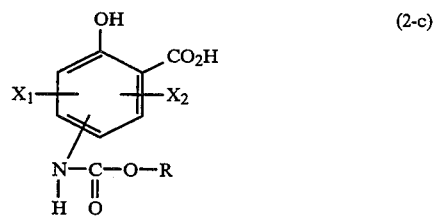
(2-c)

wherein $X_1$ and $X_2$ are a hydrogen atom, a halogen atom, an alkyl group, an alkoxy group, an aralkyl group or an aryl group, and R is an alkyl group, alkenyl group, an aralkyl group or an aryl group, or a metal salt of the salicylic acid derivative.

3. The heat-sensitive recording material of claim 2 wherein the aliphatic amide compound is represented by the formula (3):

$$R_3CONH_2 \qquad (3)$$

wherein $R_3$ is an alkyl group or an alkenyl group and has 17~59 carbon atoms.

4. The heat-sensitive recording material of claim 2 wherein the aliphatic amide compound is represented by the formula (4):

$$R_4CONHR_5 \qquad (4)$$

wherein $R_4$ is an alkyl group or an alkenyl group, $R_5$ is an alkyl group, an alkenyl group or a hydroxymethyl group, and the sum of carbon atoms in $R_4$ and $R_5$ is 17~59.

5. The heat-sensitive recording material of claim 2 wherein the aliphatic amide compound is represented by the formula (5):

$$R_6CONHR_7NHOCR_6 \qquad (5)$$

wherein $R_6$ is an alkyl group or an alkenyl group, $R_7$ is a divalent aliphatic group, and the sum of carbon atoms in $R_6$ and $R_7$ is 16~58.

6. The heat-sensitive recording material of claim 2 wherein the aliphatic amide compound is represented by the formula (6):

$$R_8NHOCR_9CONHR_8 \qquad (6)$$

wherein $R_8$ is an alkyl group or an alkenyl group, $R_9$ is a divalent aliphatic group, and the sum of carbon atoms in $R_8$ and $R_9$ is 16~58.

7. The heat-sensitive recording material of claim 2 wherein the metal salt of the salicylic acid derivative represented by the formula (1-c) is a zinc salt.

8. The heat-sensitive recording material of claim 2 wherein the amount of the aliphatic amide compound is 10~300% based on the salicylic acid derivative or the metal salt of said derivative.

9. The heat-sensitive recording material of claim 2, wherein the electron accepting compound comprises one or more divalent, trivalent or tetravalent metal salts of said salicylic acid derivative of formula (2-c).

10. The heat-sensitive recording material of claim 2, wherein the $X_1$ and $X_2$ in the salicylic acid derivative of formula (2-c) or metal salt of said salicylic acid derivative are hydrogen, $C_1$–$C_{20}$ alkyl, $C_5$–$C_{14}$ alicyclic group, $C_1$–$C_{20}$ alkoxy, $C_7$–$C_{20}$ aralkyl, phenyl, fluorine, chlorine or bromine.

11. The heat-sensitive recording material of claim 2, wherein the electron accepting compound comprises one or more metal salts of said salicylic acid derivative of formula (2-c) selected from the group consisting of sodium, potassium, lithium, zinc, cadmium, mercury, magnesium, calcium, barium, nickel, tin, gallium, chromium, copper, molybdenum, wolfram, zirconium, strontium, manganese, cobalt, titanium, aluminum and iron salts.

12. The heat-sensitive recording material of claim 1 wherein the aliphatic amide compound is represented by the formula (3):

$$R_3CONH_2 \qquad (3)$$

wherein $R_3$ is an alkyl group or an alkenyl group and has 17~59 carbon atoms.

13. The heat-sensitive recording material of claim 1 wherein the aliphatic amide compound is represented by the formula (4):

$$R_4CONHR_5 \qquad (4)$$

wherein $R_4$ is an alkyl group or an alkenyl group, $R_6$ is an alkyl group, an alkenyl group or a hydroxymethyl group, and the sum of carbon atoms in $R_4$ and $R_6$ is 17~59.

14. The heat-sensitive recording material of claim 1 wherein the aliphatic amide compound is represented by the formula (5):

$$R_6CONHR_7NHOCR_6 \qquad (5)$$

wherein $R_6$ is an alkyl group or an alkenyl group, $R_7$ is a divalent aliphatic group, and the sum of carbon atoms in $R_6$ and $R_7$ is 16~58.

15. The heat-sensitive recording material of claim 1 wherein the aliphatic amide compound is represented by the formula (6):

$$R_8NHOCR_9CONHR_8 \qquad (6)$$

wherein $R_8$ is an alkyl group or an alkenyl group, $R_9$ is a divalent aliphatic group, and the sum of carbon atoms in $R_8$ and $R_9$ is 16~58.

16. The heat-sensitive recording material of claim 1 wherein the metal salt of the salicylic acid derivative represented by the formula (1) is a zinc salt.

17. The heat-sensitive recording material of claim 1 wherein the amount of the aliphatic amide compound is 10~300% by weight based on the salicylic acid derivative or the metal salt of said derivative.

18. The heat-sensitive recording material of claim 1, wherein the electron accepting compound comprises one or more divalent, trivalent or tetravalent metal salts of said salicylic acid derivative of formula (1).

19. The heat-sensitive recording material of claim 1, wherein the $X_1$ and $X_2$ in the salicylic acid derivative of formula (1) or metal salt of said salicylic acid derivative are hydrogen, $C_1$–$C_{20}$ alkyl, $C_5$–$C_{14}$ alicyclic group, $C_1$–$C_{20}$ alkoxy, $C_7$–$C_{20}$ aralkyl, phenyl, fluorine, chlorine or bromine.

20. The heat-sensitive recording material of claim 1, wherein the electron accepting compound comprises one or more metal salts of said salicylic acid derivative of formula (1) selected from the group consisting of sodium, potassium, lithium, zinc, cadmium, mercury, magnesium, calcium, barium, nickel, tin, gallium, chromium, copper, molybdenum, wolfram, zirconium, strontium, manganese, cobalt, titanium, aluminum and iron salts.

* * * * *